US00PP21209P2

(12) United States Plant Patent
Van Den Top

(10) Patent No.: US PP21,209 P2
(45) Date of Patent: Aug. 17, 2010

(54) *HOSTA* PLANT NAMED 'TROPICAL DANCER'

(50) Latin Name: ***Hosta* hybrid (Tratt.)**
Varietal Denomination: Tropical Dancer

(76) Inventor: Hendrik Jan Van Den Top, Wesselseweg 46, 3771 PC Barneveld (NL)

( * ) Notice: Subject to any disclaimer, the term of this patent is extended or adjusted under 35 U.S.C. 154(b) by 99 days.

(21) Appl. No.: 12/287,537

(22) Filed: Oct. 10, 2008

(51) Int. Cl.
*A01H 5/00* (2006.01)

(52) U.S. Cl. ..... Plt./353

(58) Field of Classification Search ..... Plt./353
See application file for complete search history.

(56) References Cited

U.S. PATENT DOCUMENTS

PP17,294 P2 * 12/2006 Hansen ..... Plt./353

* cited by examiner

*Primary Examiner*—Wendy C. Haas
(74) *Attorney, Agent, or Firm*—Audrey Charles

(57) ABSTRACT

A new and distinct cultivar of *Hosta* plant named 'Tropical Dancer', characterized by its broadly spreading foliage with upright flower scapes, widely-margined light yellow and green variegated foliage, violet-colored flowers that are positioned above the foliage on strong scapes, and good garden performance.

2 Drawing Sheets

Latin name of genus and species of plant claimed: *Hosta* hybrid (Tratt.).

Variety denomination: 'Tropical Dancer'.

BACKGROUND OF THE INVENTION

The present invention relates to a new and distinct cultivar of *Hosta* plant botanically known as *Hosta* hybrid and hereinafter referred to by the cultivar name 'Tropical Dancer'.

The new *Hosta* cultivar is a naturally-occurring sport of 'Spring Fling', not patented, characterized by its green heart-shaped leaves with a wavy, creamy white margin. The new cultivar was discovered as a whole plant and selected during July 2004 in a controlled environment at Barneveld, The Netherlands.

Asexual reproduction of the new *Hosta* by division and tissue culture in a controlled environment in Barneveld, The Netherlands since 2004, has shown that the unique features of this new *Hosta* are stable and reproduced true to type in successive generations.

SUMMARY OF THE INVENTION

The following characteristics of the new cultivar have been repeatedly observed and can be used to distinguish 'Tropical Dancer' as a new and distinct cultivar of *Hosta* plant:

1. Broadly spreading foliage with upright flower scapes;
2. Widely-margined light yellow and green variegated foliage;
3. Violet-colored flowers that are positioned above the foliage on strong scapes; and
4. Good garden performance.

Of the many commercially available *Hosta* cultivars, the most similar in comparison to the new cultivar is the parent cultivar 'Spring Fling', not patented. However, in side by side comparisons, plants of the new cultivar differ from its parent, in leaf color and width of the leaf margin.

BRIEF DESCRIPTION OF THE DRAWINGS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tropical Dancer'. The plants were grown outdoors in 3 liter containers for approximately 1 year in Barneveld, The Netherlands.

The photograph on the first sheet is a side perspective view of typical plants of 'Tropical Dancer' grown in an outdoor nursery.

The photograph at the top of the second sheet is a close-up view of a typical leaf of 'Tropical Dancer'.

The photograph at the bottom of the second sheet is a close-up view of a typical inflorescence of 'Tropical Dancer'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in June 2008 under natural light conditions in Barneveld, The Netherlands when day temperatures ranged from 12° C. to 31° C. (53° F. to 88° F.) and night temperatures ranged from 4° C. to 16° C. (39° F. to 61° F.).

Plants used in the following description were grown in Barneveld, The Netherlands, in an outdoor nursery in 3 liter containers and under conditions which closely approximate commercial production conditions. The plants were grown for approximately 1 year when the description was taken. Measurements and numerical values represent averages of typical plants.

Botanical classification: *Hosta* hybrid cultivar Tropical Dancer.

Parentage: Naturally-occurring sport of *Hosta* hybrid 'Spring Fling', not patented.

Propagation:

*Type.*—In vitro propagation utilizing typical methods for *Hosta* is preferred, garden division is also possible.

*Time to initiate roots.*—Approximately 20 days at a temperature of approximately 15° C.

*Time to produce a rooted plant.*—Approximately 50 days at a temperature of approximately 15° C.

*Root description.*—Medium thickness, fibrous; creamy white in color.

*Rooting habit.*—Moderately branching, moderate density.

Plant description:

*Growth habit and general appearance.*—Herbaceous flowering perennial plant. Broadly spreading foliage with upright flower scapes. Flowering stems and leaves basal rosettes; moderately vigorous growth habit. Violet-colored flowers are positioned above the foliage on strong scapes.

*Crop time.*—Approximately 20 weeks from tissue culture plantlets to finish in an 11 cm container.

*Size.*—Plant height (soil level to top of foliar plane): Approximately 29.7 cm. Plant height (soil level to top of inflorescences): Approximately 75.2 cm. Plant width (spread): Approximately 69.4 cm.

Foliage description:

*General description.*—Leaves basal, simple with approximately 7 per basal rosette, generally symmetrical and long-persisting.

*Leaves.*—Shape: Ovate to slightly carinate. Appearance: Slightly glossy. Apex: Apiculate. Base: Obtuse to attenuate. Margin: Entire, very wavy. Length: Approximately 26.6 cm. Width: Approximately 14.2 cm. Texture of upper and lower surfaces: Smooth, glabrous; furrowed on venation. Venation pattern: Camptodrome. Color of upper surface of young foliage: 144A with a lighter margin of 144C. Color of lower surface of young foliage: 147C with a lighter margin of 147D. Color of upper surface of mature foliage: 137A and 143A with margins of 4C to 4D. Color of lower surface of mature foliage: 191B with margins of 150D to 2D. Color of upper and lower surfaces of venation: Indistinguishable from leaf color.

*Petiole.*—Length: Approximately 23.4 cm. Diameter: Approximately 61.4 cm. Texture of upper and lower surfaces: Smooth, glabrous. Color of upper and lower surfaces: 137C with margins of 155A to 157D.

Flowering description:

*Natural flowering season.*—Continuously flowering from June into August in Barneveld, The Netherlands.

*Lastingness of individual flower on the plant.*—Approximately 5 days, not persistent.

Inflorescence description:

*General description.*—Terminal racemes with flowers facing outward or slightly downward. Freely flowering habit with about 32 flowers developing per inflorescence. Fragrance: None detected. Inflorescence height: Approximately 28.5 cm. Inflorescence diameter: Approximately 10.2 cm.

*Peduncles (scapes).*—Strength: Strong. Length: Approximately 27.7 cm. Diameter: Approximately 4.0 mm. Angle: Erect. Texture: Smooth, glabrous. Color: 143A to 144A.

Flower description:

*Type.*—Campanulate, single.

*Flower buds.*—Rate of opening: Per flowering stem, approximately 8% of the flowers open together with all flowers per inflorescence opening within approximately 4 weeks. Shape: Oblanceolate. Length: Approximately 3.2 cm. Diameter: Approximately 9.0 mm. Color: 85D.

*Perianth.*—Depth: Approximately 4.5 cm. Diameter: Approximately 3.8 cm.

*Tepals.*—Quantity: 6, arranged in a single whorl of three narrow tepals and 3 wider tepals, fused at base with upper 50% free. Shape: Oblanceolate. Appearance: Dull. Margin: Entire. Apex: Acute. Length: Approximately 4.2 cm. Width of narrow tepals: Approximately 9.0 mm. Width of wider tepals: Approximately 1.3 cm. Texture of upper and lower surfaces: Smooth, glabrous. Color of upper (inner) surface when first and fully open: Purer white than 155D with stripes of 85D to lighter than 85D. Color of lower (outer) surface when first open: Almost pure white with stripes of 85D and lighter than 85D. Color of lower (outer) surface when fully open: Almost pure white with stripes of 85D and lighter than 85D, fading to N155C with senescence.

*Bracts.*—Quantity: One per flower at the base of the pedicel. Length: Approximately 2.9 cm. Width: Approximately 1.0 mm. Shape: Narrowly ovate, concave. Apex: Narrow acute. Base: Cuneate. Margin: Entire. Texture, upper and lower surfaces: Smooth, glabrous. Color, upper and lower surfaces: 144B to 144C.

*Pedicels.*—Length: Approximately 9.0 mm. Diameter: Approximately 1.0 mm. Angle: Approximately 60° from vertical. Strength: Strong. Texture: Smooth, glabrous. Color: 146A.

*Reproductive organs.*—Androceium: Quantity per flower: Typically six; anthers dorsifixed. Filament length: Approximately 4.1 cm, curled. Filament color: 157A. Anther shape: Narrowly oblong. Anther length: Approximately 4.0 mm. Anther color: N187A. Pollen amount: Sparse. Pollen color: 12B. Gynoecium: Pistils: Quantity per flower: One. Pistil length: Approximately 4.1 cm. Stigma shape: Crested. Stigma color: 155C. Style length: Approximately 4.0 cm. Style color: 155D tinged with N157A to 145B at base. Ovary color: 145A.

Seed and fruit production: Seed and fruit development have not been observed.

Disease and pest resistance: Plants of the new *Hosta* have not been noted to be resistant to pathogens and pests common to *Hosta*.

Garden performance: Plants of the new *Hosta* have been observed to have good garden performance and tolerate rain, wind and high temperatures of about 35° C. (95° F.). Plants of the new *Hosta* have been observed to be hardy to a least USDA Zone 5.

What is claimed is:

1. A new and distinct cultivar of *Hosta* plant named 'Tropical Dancer', substantially as herein shown and described.

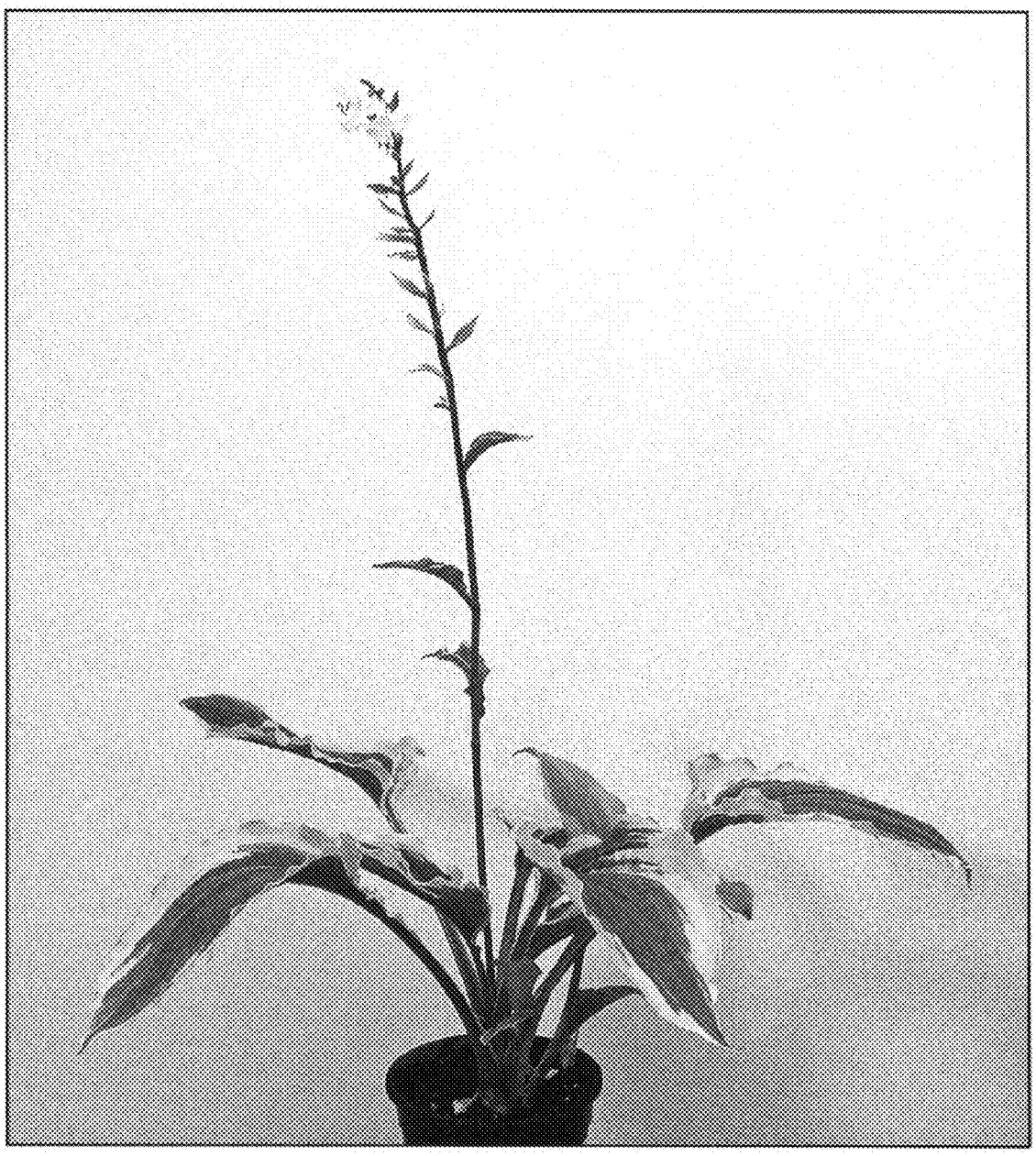

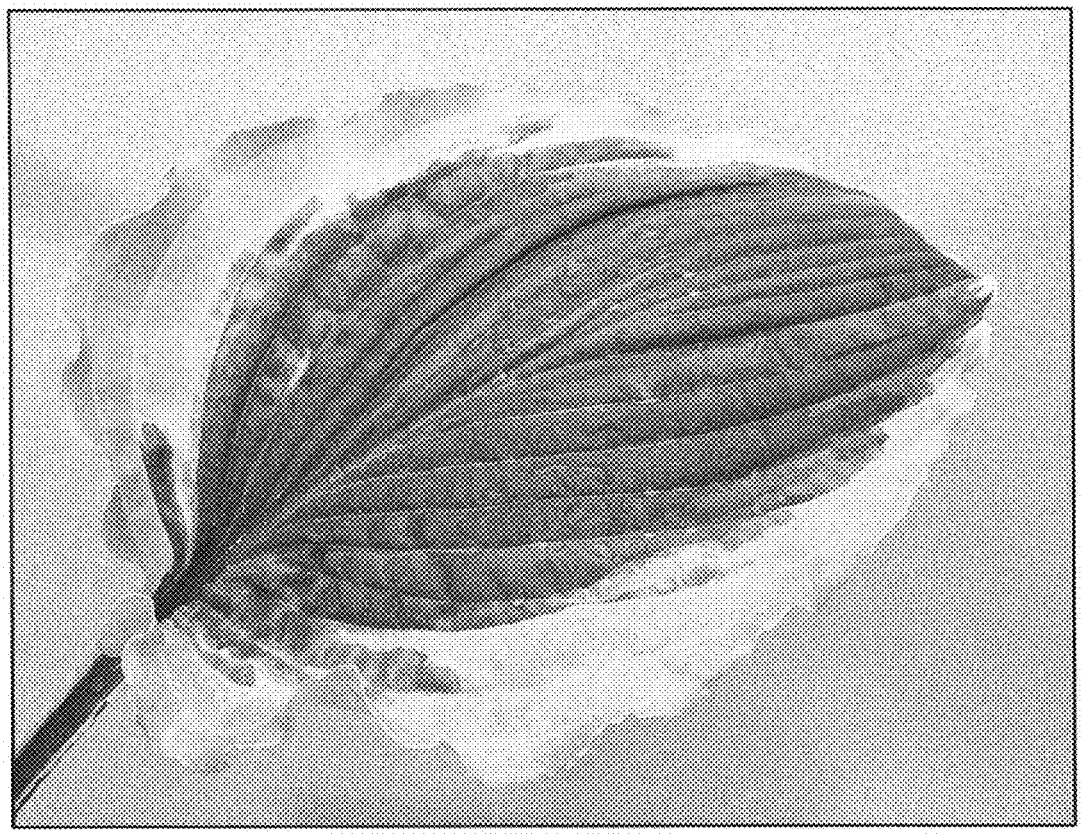
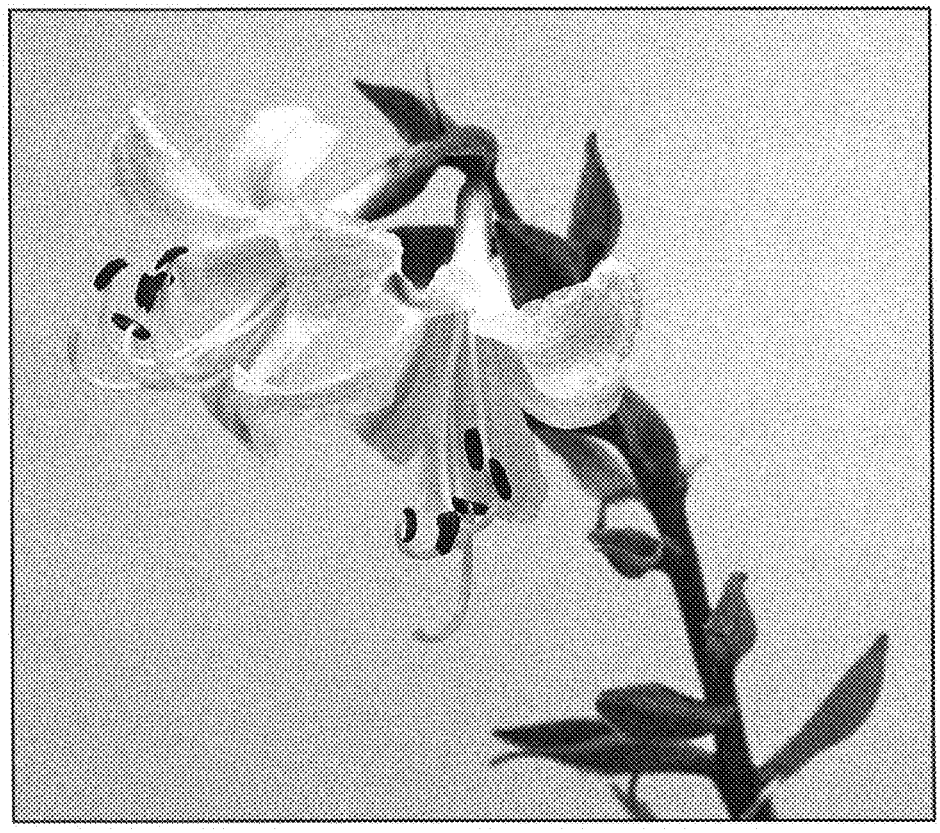

* * * * *